United States Patent
Den Boestert et al.

(10) Patent No.: US 12,378,212 B2
(45) Date of Patent: Aug. 5, 2025

(54) PROCESS FOR REMOVING POLY(PROPYLENE OXIDE) FROM PROPYLENE OXIDE BY MEMBRANE SEPARATION

(71) Applicant: SHELL USA, INC., Houston, TX (US)

(72) Inventors: Johannes Leendert Willem Cornelis Den Boestert, Amsterdam (NL); Adrianus Robert Storm, Moerdijk (NL)

(73) Assignee: SHELL USA, INC., Houston, TX (US)

( * ) Notice: Subject to any disclaimer, the term of this patent is extended or adjusted under 35 U.S.C. 154(b) by 641 days.

(21) Appl. No.: 17/769,790

(22) PCT Filed: Nov. 16, 2020

(86) PCT No.: PCT/EP2020/082227
§ 371 (c)(1),
(2) Date: Apr. 18, 2022

(87) PCT Pub. No.: WO2021/099255
PCT Pub. Date: May 27, 2021

(65) Prior Publication Data
US 2022/0380327 A1      Dec. 1, 2022

(30) Foreign Application Priority Data
Nov. 20, 2019   (EP) .................................... 19210455

(51) Int. Cl.
*C07D 301/32*        (2006.01)
(52) U.S. Cl.
CPC .................. *C07D 301/32* (2013.01)

(58) Field of Classification Search
CPC ........................................................ C07D 301/32
USPC .............................................................. 549/541
See application file for complete search history.

(56) References Cited

U.S. PATENT DOCUMENTS

| | | |
|---|---|---|
| 4,692,535 A | 9/1987 | Larson et al. |
| 5,093,002 A | 3/1992 | Pasternak |
| 5,102,551 A | 4/1992 | Pasternak |
| 5,150,118 A | 9/1992 | Finkle et al. |
| 5,248,794 A | 9/1993 | Chappell et al. |
| 5,275,726 A | 1/1994 | Feimer et al. |

(Continued)

FOREIGN PATENT DOCUMENTS

| | | |
|---|---|---|
| GB | 2348200 A | 9/2000 |
| WO | 9627430 A1 | 9/1996 |

(Continued)

OTHER PUBLICATIONS

Wikipedia (Mesh (scale), Oct. 24, 2018, p. 1-3). (Year: 2018).*

(Continued)

*Primary Examiner* — Taylor V Oh
(74) *Attorney, Agent, or Firm* — SHELL USA, INC.

(57) ABSTRACT

The invention relates to a process for removing 5poly (propylene oxide) from propylene oxide, comprising: a) sending a stream comprising propylene oxide and poly (propylene oxide) to a filtration screen having openings with an average diameter of at most 50 μm; and b) sending the filtrate stream resulting from step a) to a membrane 10 having an average pore size of from 0 to 30 nm and recovering a permeate stream from the membrane as a purified propylene oxide stream.

6 Claims, 1 Drawing Sheet

(56) References Cited

U.S. PATENT DOCUMENTS

| | | |
|---|---|---|
| 5,362,401 A | 11/1994 | Whetsel |
| 5,458,774 A | 10/1995 | Mannapperuma |
| 6,462,209 B1 | 10/2002 | Beckers et al. |
| 7,722,758 B2 | 5/2010 | Den Boestert et al. |
| 8,304,564 B2 | 11/2012 | Beckers et al. |
| 8,608,939 B2 | 12/2013 | Den Boestert et al. |

FOREIGN PATENT DOCUMENTS

| | | | |
|---|---|---|---|
| WO | WO 0055148 | * | 9/2000 |
| WO | WO 2008074791 A1 | * | 6/2008 |

OTHER PUBLICATIONS

Office Action Received for Singapore Application No. 11202204203U, Mailed on Dec. 1, 2023, 05 Pages(05 pages of Official Copy).

"Nanofiltration: Teacher Materials", Nanosense, Retrieved from internet: "https://web.archive.org/web/20160910150510/https:/nanosense.sri.com/activities/finefilters/nanofiltration/FF_Lesson3Teacher.pdf", 41 Pages.

"Methods To Reduce Membrane Fouling", Synder Filtration, Retrieved from internet: "https://synderfiltration.com/learning-center/articles/membranes/methods-to-reduce-membrane-fouling/", 2 Pages.

International Search Report and Written Opinion received for PCT Patent Application No. PCT/EP2020/082227, mailed on Dec. 16, 2020, 9 pages.

Oertel, "Polyurethane Handbook: Chemistry—Raw Materials—Processing—Application—Properties", 1985, 3 Pages.

Othmer, "Encyclopedia of Chemical Technology", 4th Edition, vol. 16, Oct. 13, 1995, pp. 158-164.

Office Action Received for Chinese Application No. 202080079765.2, Mailed on Apr. 21, 2023, 14 Pages (8 Pages of English Translation and 6 Pages of Official Copy).

* cited by examiner

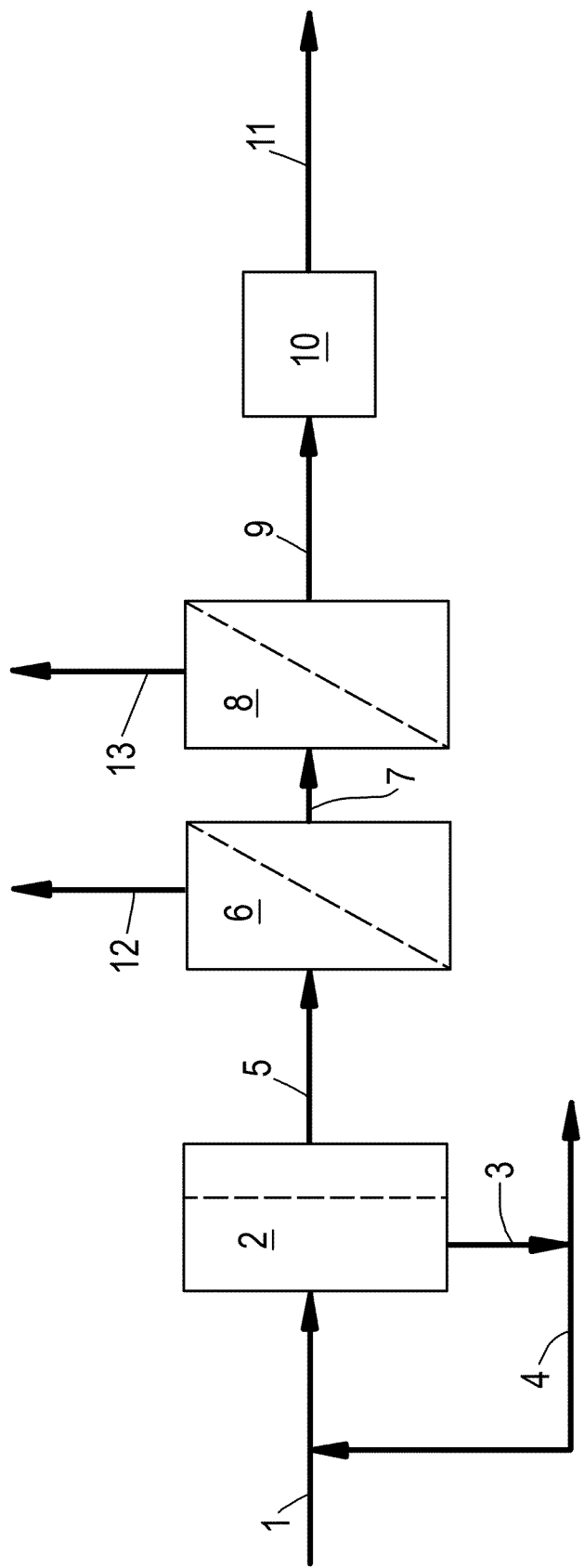

PROCESS FOR REMOVING POLY(PROPYLENE OXIDE) FROM PROPYLENE OXIDE BY MEMBRANE SEPARATION

CROSS REFERENCE TO RELATED APPLICATIONS

This is a National stage application of International application No PCT/EP2020/082227, filed 16 Nov. 2020, which claims priority of EP Application Serial No. 19210455.2, filed 20 Nov. 2019 which is incorporated herein by reference in its entirety.

FIELD OF THE INVENTION

The present invention relates to a process for removing poly(propylene oxide) from propylene oxide by membrane separation.

BACKGROUND OF THE INVENTION

Propylene oxide is widely used as precursor for preparing polyether polyols, which upon reaction with polyisocyanate compounds yield polyurethanes. The quality of the propylene oxide has significant impact on the quality of the polyurethane foams eventually obtained, especially when these foams are high resilience flexible polyurethane foams. Particularly the presence of poly(propylene oxide) is known to cause undesired effects in the polyurethane foam formation. Examples of such undesired effects are the occurrence of blow holes, low foam rise and even collapse of the foam formed. Particularly, in moulding applications, the presence of poly(propylene oxide) in the propylene oxide used for preparing the starting polyether polyol may cause problems in terms of quality of the polyurethane foam. The presence of poly(propylene oxide) in propylene oxide used for preparing a polyether polyol for making slabstock polyurethane foams, may be less problematic.

In producing slabstock polyurethane foams, slabs of polyurethane foam are produced continuously or discontinuously as semi-finished products and are finally cut to the required size and shape. The characteristic feature of moulded polyurethane foams in which they fundamentally differ from slabstock polyurethane foams, is the manner of their production. This proceeds by reaction of the polyurethane raw materials in moulds. The finished moulded product no longer has to be cut to the required size and shape. For a further description of the differences between slabstock and moulded polyurethane foams, reference is made to handbooks on polyurethane foams, such as "Polyurethane Handbook/Chemistry—Raw Materials—Processing—Application—Properties" by Gunter Oertel (Carl Hanser Verlag, Munich 1985).

It has appeared in practice that, in general, where propylene oxide is to be used to prepare a polyether polyol for making moulded polyurethane foams, no more than 1 ppm of poly(propylene oxide) should be present in said propylene oxide. If more propylene oxide is present, one or more of the above-mentioned undesired effects may occur when making the foam. On the other hand, where propylene oxide is to be used to prepare a polyether polyol for making slabstock polyurethane foams, in general, up to 3 ppm of poly(propylene oxide) may be present in the propylene oxide.

Methods for manufacturing propylene oxide are well known in the art. Commercial production normally takes place via the chlorohydrin process or via the hydroperoxide process. In the latter process propene is reacted with an organic hydroperoxide. This hydroperoxide is either tert-butyl hydroperoxide or ethylbenzene hydroperoxide. In the first case tert-butyl alcohol is formed as a co-product (to be further converted into methyl tert-butyl ether), in the second case styrene is formed as the co-product. In the chlorohydrin process chlorine, propene and water are reacted to form propylene chlorohydrin, which is subsequently dehydrochlorinated with calcium hydroxide to form propylene oxide. For the purpose of the purification of propylene oxide it is immaterial which preparation route is used. Namely, in all processes poly(propylene oxide) is formed in undesirably high quantities. Moreover, it is known (e.g. from U.S. Pat. No. 4,692,535) that high molecular weight poly(propylene oxide) may be formed during storage or transport, for example upon contact with a metal and/or metal oxide, such as metal oxide of carbon steel.

It is known to remove poly(propylene oxide) from propylene oxide by membrane separation. One method for purification of propylene oxide by membrane separation is disclosed in WO2008074791. In the process of said WO2008074791, poly(propylene oxide) is removed from propylene oxide by using a membrane having an average pore size of from 0 to 5 nm.

One way of determining the suitability of a membrane for separating poly(propylene oxide) (PPO) from propylene oxide, is by calculating the PPO rejection, as follows:

PPO rejection (%)=$(1-([PPO]_p/[PPO]_f))*100$ wherein $[PPO]_p$ is the poly(propylene oxide) concentration in the permeate and $[PPO]_f$ is the poly(propylene oxide) concentration in the feed. Where in the present specification reference is made to PPO rejection, the PPO rejection defined in the above way is meant.

In the process of above-mentioned WO2008074791, a relatively high PPO rejection is achieved. However, an impure propylene oxide feed may also contain other impurities, in addition to poly(propylene oxide). Such other impurities may comprise relatively large particles, which may have a particle size in the range of from 5 to 20 μm, such as rust particles resulting from corrosion of tanks and pipelines, PPO particulates and combinations thereof. If these large particles are not removed first, fouling of any subsequent membrane may occur. Such membrane may become clogged relatively fast, in which case the membrane should be cleaned relatively frequently or should even be replaced, which causes the membrane separation equipment to be out of operation for a relatively large part of the time. In addition to such fouling and clogging, rust particles may catalyze the formation of additional PPO from the propylene oxide to be purified, which is also undesired.

Further, it is desired to provide a process for purification of such impure propylene oxide involving the use of a membrane, which process can be applied to provide pure propylene oxide of a certain constant quality (purity), irrespective of whether impure propylene oxide having a relatively low or high PPO concentration is fed to that process. This would enhance process flexibility and operational robustness. For in a case where the impure propylene oxide feed has a high PPO concentration, the PPO concentration in the permeate may still be too high despite a relatively high PPO rejection. In the future, specifications on the allowable maximum content of PPO in propylene oxide may become more stringent. Thus, the lower the content of PPO in purified propylene oxide, the higher the value of that propylene oxide product, especially when specifications on PPO content are or become (more) stringent.

Therefore, it is an object of the present invention to provide a process for removing poly(propylene oxide) from propylene oxide, wherein a membrane is used, which process does not have one or more of the above-mentioned disadvantages.

SUMMARY OF THE INVENTION

Surprisingly it was found that the above object may be achieved by a process wherein a propylene oxide feed comprising poly(propylene oxide) is purified by a combination of a filtration screen having openings with an average diameter of at most 50 µm, followed by a membrane having an average pore size of from 0 to 30 nm.

Accordingly, the present invention relates to a process for removing poly(propylene oxide) from propylene oxide, comprising:

a) sending a stream comprising propylene oxide and poly(propylene oxide) to a filtration screen having openings with an average diameter of at most 50 µm; and b) sending the filtrate stream resulting from step a) to a membrane having an average pore size of from 0 to 30 nm and recovering a permeate stream from the membrane as a purified propylene oxide stream.

BRIEF DESCRIPTION OF THE DRAWING

FIG. 1 shows an embodiment of the process of the present invention.

DETAILED DESCRIPTION OF THE INVENTION

The process of the present invention comprises step a), step b) and optional step c). Said process may comprise one or more intermediate steps between steps a) and b) and between steps b) and c). Further, said process may comprise one or more additional steps preceding step a) and/or following step b) or c).

While the process of the present invention and a composition or stream used in said process are described in terms of "comprising", "containing" or "including" one or more various described steps and components, they can also "consist essentially of" or "consist of" said one or more various described steps and components.

In the context of the present invention, in a case where a composition or stream comprises two or more components, these components are to be selected in an overall amount not to exceed 100%.

Further, where upper and lower limits are quoted for a property then a range of values defined by a combination of any of the upper limits with any of the lower limits is also implied.

The term "poly(propylene oxide)" as used throughout the present specification in relation to the present invention, refers to poly(propylene oxide) having a molecular weight of 1500 Dalton or higher, or having a molecular weight of 1000 Dalton or higher, or having a molecular weight of 900 Dalton or higher, or having a molecular weight of 750 Dalton or higher, or having a molecular weight of 500 Dalton or higher, unless stated otherwise. The molecular weights as used throughout this specification are expressed in Dalton (1 Da=1 g/mole) and may be determined by size-exclusion chromatography (SEC).

Step a) of the present process comprises sending a stream comprising propylene oxide and poly(propylene oxide) to a filtration screen having openings with an average diameter of at most 50 µm. Within the present specification, the terms "filtration screen" and "filter" and "filter mesh" are used interchangeably and have the same meaning. Said impure propylene oxide feed may also contain other impurities, in addition to poly(propylene oxide). Such other impurities may comprise relatively large particles, which may have a particle size in the range of from 5 to 20 µm, such as rust particles resulting from corrosion of tanks and pipelines, PPO particulates and combinations thereof. An advantage of using a filtration screen having openings with an average diameter of at most 50 µm is that relatively large particles may first be removed, such as the above-mentioned rust particles and PPO particulates which may have a particle size in the range of from 5 to 20 µm.

The average diameter of the openings of the filtration screen used in step a) of the present process is at most 50 µm, preferably at most 40 µm, more preferably at most 30 µm, more preferably at most 25 µm, more preferably at most 20 µm, more preferably at most 15 µm, more preferably at most 10 µm, more preferably at most 5 µm, most preferably at most 2 µm, and may be at least 0.1 µm or at least 0.5 µm at least 1 µm. It is an advantage that in step a) the filtration screen, unlike membranes, can easily be tailored to the size of the contaminants to be removed by simply adjusting the mesh size, that is to say by adjusting the average diameter of the filtration screen openings. Such average diameter may be chosen such that it is below the lowest particle size of the larger particles that one wishes to remove by using the filtration screen in step a).

The filtration screen used in step a) may comprise a mesh, which may be a metal mesh or a polymeric mesh. Within the present specification, a "mesh" means a structure made of connected strands of metal, fiber or other flexible/ductile material, with evenly spaced openings between them. This may also be referred to as a "wire-mesh". The mesh may be flexible but may also be more rigid, such as a reinforced polymeric mesh. A suitable polymeric mesh material is Teflon®. For the filtration screen, fibrous material may be used, such as metal fibers, polymeric fibres and/or ceramic fibres. Preferably, any polymeric material in the filtration screen to be used in step a) is resistant to hydrocarbons, such as propylene oxide. This implies that the filtration screen does not dissolve in the propylene oxide which it has to purify.

The effective filter surface area of a filter, like the filtration screen used in step a) of the present process, is the area through which fluid can actually pass. Filters using metal mesh tend to have a relatively high effective filter surface area. Therefore, it is preferred that the filtration screen used in step a) comprises metal mesh. Further, preferably, the filtration screen comprises at least 2 mesh layers. In this way, the mesh layers provide strength to each other. In a further preferred embodiment, the filter comprises at least 2 mesh layers which have been sintered together to provide a rigid and immobilized mesh structure which gives a sharp and fixed particle separation.

Further, preferably, the filtration screen is used in step a) as a self-cleaning filtration (SCF) screen. Self-cleaning filtration may comprise a so-called "back-wash cycle" (or "back-flush cycle"). Such back-wash cycle comprises regularly changing the flow direction of fluid through the filtration screen to remove particles that had become attached to the filtration screen on the retentate side and/or which had become trapped in the openings of the filtration screen. For example, PPO/rust particulates may be relatively sticky and therefore need to be detached from the filtration screen.

Upon detachment, these particles may then be removed via a retentate outlet. Upon such removal, the normal filter cycle operation may be resumed and advantageously more effective and full use may be made of the cleaned filtration screen. In addition, any particles that may cause PPO formation, such as rust particles, have advantageously been removed at the same time.

Such change of flow direction in self-cleaning filtration may be achieved by having a cleaning fluid on the filtrate side of the filtration screen at a pressure which is higher than the pressure of the fluid to be filtered on the retentate side on said screen. This pressure difference results in that the cleaning fluid will flow through the filtration screen in a direction which is opposite to the direction of normal flow, that is to say opposite to the direction of normal flow of the fluid to be filtered. Such "normal flow" refers to non-cleaning time periods.

The cleaning fluid used in self-cleaning filtration can be any fluid known to be suitable to someone skilled in the art. A cleaning fluid which is especially preferred is filtrate resulting from step a) of the present process. It is especially advantageous to use filtrate for cleaning the filtration screen by which the filtrate has been obtained because in that way no additional compounds are introduced. This allows easy operation and reduced risk of contamination.

The above-mentioned pressure difference may be achieved by reducing the pressure of the fluid to be filtered on the retentate side of the filtration screen to a pressure which is below the pressure of a cleaning fluid on the filtrate side of the filtration screen. Such reduction in pressure can comprise removing overpressure or reducing the pressure to below atmospheric pressure. As the remainder of a filter unit comprising the filtration screen generally is at substantially more than atmospheric pressure, it often suffices to lower the pressure of a retentate outlet to atmospheric pressure.

A back-wash (or back-flush) in self-cleaning filtration may be triggered in a variety of ways. For example, a back-wash may be initiated once the pressure of the fluid to be filtered on the retentate side of the filtration screen reaches a certain threshold, for example 0.5 bar, because of relatively large particles blocking a portion of the openings of the filtration screen. This is preferred in a case where the feed contains a relatively high amount of such large particles and/or where particles, such as poly(propylene oxide) particles, are sticky and prone to penetrate (be dragged) into and thereby also block the openings of the filtration screen. A pressure-based self-cleaning back-wash is preferred as in such case there is a minimal back-wash usage due to its back-wash efficiency. In conventional (non-self-cleaning) back-wash, a substantially higher volume of washing solvent is to be used to achieve the same effect. In case the feed contains a relatively low amount of such large particles and/or sticky particles, a timer-based self-cleaning back-wash (e.g. once per hour) may be more suitable.

Thus, an advantage of using self-cleaning filtration screens in step a) of the present process is that the frequency of the back-wash may be determined on the basis of the specific feed, that is to say the specific stream comprising propylene oxide and poly(propylene oxide) to be purified. For example, the back-wash frequency may be determined by the relative amount of large particles to be removed from the feed. That is to say, the higher such amount the higher the back-wash frequency should generally be. Another relevant factor is the relative "stickiness" of the particles in such feed. A higher back-wash frequency is generally needed to remove PPO/rust particulates which may be relatively sticky.

Another advantage of using self-cleaning filtration screens in step a) of the present process is that there is no exposure to propylene oxide, which exposure is however a risk for example when manually replacing cartridge filters (which are not self-cleaning). Therefore, using self-cleaning filtration screens is beneficial to HSSE aspects in purifying propylene oxide (HSSE=Health Safety Security Environment).

Furthermore, when using self-cleaning filtration screens in step a) of the present process, more propylene oxide may end up in the retentate stream resulting from step a). However, this loss of propylene oxide may be minimized by minimizing the back-wash duration and/or back-wash frequency, for example by applying a relatively large pressure difference during a back-wash. Besides, such retentate stream comprising more propylene oxide may suitably be used as raw material in making a polyether polyol to be used in making slabstock polyurethane foam.

Filtration screens (filters) for use in step a) of the present process can be obtained from the company Filtrex s.r.l., Italy. A filter which has been found to be especially suitable is the filter known as the Automatic Counterwash Refining (ACR) filter which is commercially available from this company.

A preferred filter unit that may be used in step a) of the present process is a filter unit as described in WO2010070029, the disclosure of which is herein incorporated by reference. Said preferred filter unit comprises a perforated tube surrounded by hollow longitudinal projections comprising a filter having openings of at most 100 micrometer diameter in which the internal space of each of the hollow projections is in fluid communication with the inside of the perforated tube and which filter is regularly subjected to cleaning by treating each of the projections with cleaning fluid wherein the flow of cleaning fluid is opposite to the direction of normal flow. Such filter unit may be as described and may be used in a way as described at page 2, line 21 to page 5, line 24 of WO2010070029, the disclosure of which passage from WO2010070029 is herein incorporated by reference.

The way in which the propylene oxide to be purified, that is to say the stream comprising propylene oxide and poly(propylene oxide) that is treated in step a), in accordance with the present invention is prepared, is immaterial to the present invention. Any known preparation process may have been applied. The propylene oxide to be treated in the process according to the present invention may be the product directly obtained from the known preparation processes. Alternatively, said directly obtained propylene oxide also may have been subjected to conventional purification and recovery techniques before it is treated in accordance with the present invention. Assuming that the propylene oxide is produced in a hydroperoxide process, such purification and recovery techniques typically involve the removal of unreacted propene and organic hydroperoxide, by-products (like propane, aldehydes and alcohol) and other treating agents. Typically, the propylene oxide feed to be purified in the present process, has been obtained by the epoxidation of propene using ethylbenzene hydroperoxide as the oxidant, then separating propene from the product mixture comprising propylene oxide and methyl phenyl carbinol, and finally separating propylene oxide from the methyl phenyl carbinol.

In general, the propylene oxide stream to be treated in step a) of the process of the present invention comprises at least 95 wt % of propylene oxide.

If the propylene oxide product to be treated in step a) is a relatively crude propylene oxide stream, such product may contain 5% by weight or less of poly(propylene oxide) based on total weight of the product. However, the present method is particularly suitable when the propylene oxide product to be treated contains 3% by weight or less, suitably 1% by weight or less, and more suitably 0.1% by weight or less of the poly(propylene oxide).

If the propylene oxide product to be treated is a relatively pure propylene oxide stream, such product preferably contains less than 500 ppmw, suitably less than 300 ppmw, more suitably less than 200 ppmw, more suitably less than 100 ppmw, more suitably less than 50 ppmw, and most suitably less than 20 ppmw of poly(propylene oxide). Typically, such relatively pure propylene oxide inlet stream comprises 1 to 15 ppmw of poly(propylene oxide).

Step b) of the present process comprises sending the filtrate stream resulting from step a) to a membrane having an average pore size of from 0 to 30 nm, and recovering the resulting permeate stream as a purified propylene oxide stream.

The membrane used in step b) may either be a non-porous membrane (no pores) or a nanofiltration membrane (pores having an average size of at most 30 nm). As further discussed below, such non-porous and nanofiltration membranes are commonly referred to in the art as dense membranes and work in a similar way.

Preferably, the membrane to be used in step b) is resistant to hydrocarbons, such as propylene oxide. This implies that the membrane does not dissolve in the propylene oxide which it has to purify.

In general, in a process for removing poly(propylene oxide) from propylene oxide by membrane separation as in step b) of the present invention, a liquid feed comprising propylene oxide and poly(propylene oxide), which in the present invention is the filtrate stream resulting from step a), is separated by the membrane into a permeate comprising propylene oxide and either no poly(propylene oxide) or poly(propylene oxide) at a concentration which is lower than the poly(propylene oxide) concentration in the feed, and a retentate comprising propylene oxide and poly(propylene oxide) at a concentration which is higher than the poly(propylene oxide) concentration in the feed.

When using a non-porous or nanofiltration membrane, very good and stable separation results are obtained in such process for removing poly(propylene oxide) from propylene oxide, as was demonstrated in above-mentioned WO2008074791. For example, less fouling of the membrane occurs and therefore the membrane has to be taken out of operation less frequently than when using an ultrafiltration membrane. Therefore, step b) of the present process can be performed efficiently on a continuous basis.

The non-porous or nanofiltration membrane to be used in step b) may be of the ceramic or polymeric type. Preferably, the membrane used is hydrophobic because the stream to be treated is a hydrocarbon stream which should be capable of passing through the membrane. An additional advantage of using a hydrophobic membrane rather than a hydrophilic one, is that using a hydrophobic membrane will prevent water from passing the membrane and entering the permeate. It is well known that water may initiate polymerisation of propylene oxide, resulting in a polyol, which is undesired.

Non-porous and nanofiltration membranes are commonly referred to in the art as dense membranes. Examples of non-porous and nanofiltration membranes are reverse osmosis type membranes. Non-porous and nanofiltration membranes should be distinguished from ultrafiltration membranes which are always porous. Ultrafiltration membranes have an average pore size of greater than 30 nm up to about 800 nm. Where nanofiltration membranes are used which are porous, they have an average membrane pore size which is at most 30 nm (nanoporous membranes). Where such nanofiltration or nanoporous membrane is used in accordance with the present invention, the average membrane pore size is suitably less than 30 nm, preferably at most 25 nm, more preferably at most 20 nm, more preferably at most 15 nm, more preferably at most 10 nm, more preferably at most 5 nm, more preferably less than 5 nm, more preferably at most 3 nm, more preferably at most 2 nm, more preferably at most 1 nm, more preferably at most 0.7 nm, more preferably at most 0.5 nm, more preferably at most 0.3 nm, more preferably at most 0.1 nm, more preferably at most 0.05 nm, and most preferably at most 0.01 nm.

Non-porous and nanofiltration membranes as such are known in the art and in principle any non-porous or nanoporous membrane capable of retaining 80% by weight or more, preferably 90% by weight or more, most preferably 95% by weight or more, and very highly preferably 99% by weight or more of the poly(propylene oxide), can be used in the present invention. The upper limit for the molecular weight of the poly(propylene oxide) to be removed, is not critical and may be as high as 500,000.

In a preferred embodiment of the present invention, the non-porous or nanofiltration membrane is a polymeric membrane. Such polymeric membrane is preferably cross-linked to provide the necessary network for avoiding dissolution of the membrane once being in contact with propylene oxide. In general, cross-linking can be effected in several ways, for instance by reaction with cross-linking agents (chemical cross-linking) and/or by irradiation. Preferably, the membrane layer has a siloxane structure which has been cross-linked by means of irradiation, as is for example described in WO199627430.

Examples of suitable, presently available cross-linked non-porous or nanofiltration membranes are cross-linked silicone rubber-based membranes, of which the cross-linked polysiloxane membranes are a particularly useful group of membranes. Such cross-linked polysiloxane membranes are known in the art, for example from U.S. Pat. No. 5,102,551.

Typically, the polysiloxanes used contain the repeating unit —Si—O—, wherein the silicon atoms bear hydrogen or a hydrocarbon group. Preferably the repeating units are of the formula (I)

$$-Si(R)(R')-O- \quad (I)$$

wherein R and R' may be the same or different and represent hydrogen or a hydrocarbon group selected from the group consisting of alkyl, aralkyl, cycloalkyl, aryl, and alkaryl. Preferably, at least one of the groups R and R' is an alkyl group, and most preferably both groups are alkyl groups, more especially methyl groups. The alkyl group may also be a 3,3,3-trifluoropropyl group. Very suitable polysiloxanes for the purpose of step b) are (—OH or —NH$_2$ terminated) polydimethylsiloxanes and polyoctylmethylsiloxanes. Thus, preferably, the polysiloxane is cross-linked. The cross-linking may be effected through a reactive terminal —OH or —NH$_2$ group of the polysiloxane. Preferred polysiloxane membranes are cross-linked elastomeric polysiloxane membranes.

Examples of suitable cross-linked elastomeric polysiloxane membranes are extensively described in above-mentioned U.S. Pat. No. 5,102,551. Thus, suitable membranes are composed of a polysiloxane polymer such as described supra having a molecular weight of 550 to 150,000, preferably 550 to 4200 (prior to cross-linking), which is cross-linked with, as cross-linking agent, (i) a polyisocyanate, or (ii) a poly(carbonyl chloride) or (iii) $R_{4-a}Si(A)_a$ wherein A is —OH, —NH$_2$, —OR, or —OOCR, a is 2, 3, or 4, and R is hydrogen, alkyl, aryl, cycloalkyl, alkaryl, or aralkyl. Further details regarding suitable polysiloxane membranes can be found in U.S. Pat. No. 5,102,551.

For the purpose of step b) the preferred non-porous membrane is a polydimethylsiloxane membrane, which is preferably cross-linked. Also other rubbery non-porous membranes could be used. In general, rubbery membranes can be defined as membranes having a non-porous top layer of one polymer or a combination of polymers, of which at least one polymer has a glass transition temperature well below the operating temperature, i.e. the temperature at which the actual separation takes place. Yet another group of potentially suitable non-porous membranes are the so called superglassy polymers. An example of such a material is poly(trimethylsilylpropyne).

The non-porous or nanofiltration membrane is typically supported on at least one porous substrate layer to provide the necessary mechanical strength. Suitably, this other porous substrate layer is made of a porous material of which the pores have an average size greater than 30 nm. Such other porous material may be a microporous, mesoporous or macroporous material which is normally used for microfiltration or ultrafiltration, such as poly(acrylonitrile). The thickness of the base layer should be sufficiently to provide the necessary mechanical strength. In addition, this substrate may in return be supported on a further porous support to provide the required mechanical strength. Typically, the thickness of the base layer is of from 100 to 250 μm, more suitably of from 20 to 150 μm. Where the non-porous or nanofiltration membrane is combined with such base layer, the membrane suitably has a thickness of from 0.5 to 10 μm, preferably of from 1 to 5 μm.

The combination of a thin top membrane layer and a thick porous support layer is often referred to as composite membranes or thin film composites. The membrane is suitably so arranged that the permeate flows first through the membrane top layer and then through the base layer, so that the pressure difference over the membrane pushes the top layer onto the base layer. Suitable porous materials for the base layer having an average pore size greater than 30 nm, are poly(acrylonitrile), poly(amideimide)+TiO$_2$, poly(etherimide), polyvinylidenedifluoride and poly(tetrafluoroethylene). Poly(acrylonitrile) is especially preferred. The preferred combination in step b) is a poly(dimethylsiloxane)-poly(acrylonitrile) combination.

The non-porous or nanofiltration membrane may also be used without a substrate layer, but it will be understood that in such a case the thickness of the membrane should be sufficient to withstand the pressures applied. A thickness greater than 10 μm may then be required. This is not preferred from a process economics viewpoint, as such thick membrane will significantly limit the throughput of the membrane, thereby decreasing the amount of purified product which can be recovered per unit of time and membrane area.

When using a non-porous or dense membrane, transmission of the permeate takes place via the solution-diffusion mechanism. The propylene oxide to be permeated dissolves in the membrane matrix and diffuses through the thin selective membrane layer, after which it desorbs at the permeate side. The main driving force for permeation is hydrostatic pressure. Examples of such membranes are reverse osmosis type membranes. In case a nanoporous membrane is used in the present invention, it is believed that separation takes place both on the basis of the above-mentioned solution-diffusion mechanism and on the basis of molecular size differences. In the latter case, there is no question of dissolution of the permeate in the membrane matrix but only of transport through the membrane via its nanopores. Where such solution-diffusion mechanism is functioning, it is believed to be important that the membrane material does not dissolve the contaminant to be removed from the membrane feed but, preferentially, only the component that has to be freed from the contaminant. The present inventors have found that especially polysiloxane membranes, for example poly(dimethylsiloxane) membranes, are capable of such preferential dissolution of propylene oxide, rather than poly(propylene oxide) which they do not dissolve.

An advantage of using non-porous membranes as compared to the use of nanoporous membranes is that there is no plugging effect. This means that there is no possibility of the membrane becoming blocked by larger molecules plugged in the pores. This could happen in porous membranes, as a result of which it is more difficult to regenerate a stable flux. Therefore, it is preferred for the purpose of step b) to use a non-porous or dense membrane. However, it is emphasised that nanoporous membranes could also be used in step b) as a nanofiltration membrane.

The retentate will still comprise valuable propylene oxide and for that reason the retentate may suitably be recycled to the membrane separation step and mixed with fresh feedstock. However, when recycling retentate, part of the retentate will have to be discharged such as to avoid build up of the poly(propylene oxide) which is to separated from the propylene oxide by means of said membrane process. Instead of recycling the retentate within the same process, it may also be subjected to a second and optionally further separation step, in which case the retentate of a first separation step is used as the feed for a second separation step.

Further, instead of recycling (part of) the retentate or further purifying it in a second and optionally further step, the retentate may also be discharged in its entirety. This is most likely advantageous where the composition of the retentate is such that it has some value as a starting material in another process, without having to further treat the retentate before such use (no further processing). The permeate has been upgraded in the sense that its contamination level has been lowered. Consequently the permeate has obtained a higher value compared to the original product. The retentate, which contains an increased proportion of poly(propylene oxide) as compared to the original product, has a value depending on the poly(propylene oxide) concentration and the perceived end use. The retentate value may be lower than or similar to the value of the original feed.

Stage cut is defined as the weight percentage of the original feed that passes through the membrane and is recovered as permeate. By adjusting the stage cut, it is possible to vary the concentration of a contaminant in the permeate, as well as the concentration of said same contaminant in the retentate. The higher the stage cut, the higher the contaminant concentration in the retentate.

In the present invention, the stage cut can vary within broad limits: 10 to 99% by weight, suitably 30 to 95% by weight or 50 to 90% by weight. All that matters is that a poly(propylene oxide) concentration in permeate and/or retentate is achieved which is below a certain maximum. For example, where it is intended to use the permeate in the production of moulded polyurethane foam, a relatively high stage cut might have to be achieved. Another relevant factor to consider is the poly(propylene oxide) concentration in the feed.

The desired stage cut can be set by varying, for a given permeability of the membrane, the trans-membrane pressure and/or the feed flow. The first option implies that, for a given feed flow, increasing the trans-membrane pressure results in a greater flux or flow of the permeate through the membrane, and therefore in a higher stage cut. According to the second option, such higher stage cut may also be achieved by decreasing the feed flow whilst maintaining a certain permeate flow through the membrane.

In step b) of the present process, the volume flux through the membrane is typically in the range of from 5 to 1000, suitably 10 to 500, and more suitably 15 to 200 l/h/m$^2$. The flux through the membrane may also be expressed as mass flux. Preferably, the flux through the membrane is constant in time. Further, the inlet stream is contacted with the membrane at a trans-membrane pressure (pressure difference) which is typically in the range of from 1 to 60 bar, suitably 3 to 35 bar, and more suitably 3 to 25 bar. The permeability of the membrane is typically in the range of from 1 to 100, suitably 2 to 50, and more suitably 3 to 10 l/h/m$^2$/bar.

In step b) of the present process, a liquid feed comprising propylene oxide and poly(propylene oxide), that is to say the filtrate stream resulting from step a), may be separated by a non-porous or nanofiltration membrane into a permeate comprising propylene oxide and either no poly(propylene oxide) or poly(propylene oxide) at a concentration which is lower than the poly(propylene oxide) concentration in the feed, and a retentate comprising propylene oxide and poly(propylene oxide) at a concentration which is higher than the poly(propylene oxide) concentration in the feed.

Preferably, the poly(propylene oxide) concentration in said permeate is from essentially zero to at most 10 ppmw (parts per million by weight), more preferably at most 5 ppmw, more preferably at most 3 ppmw, more preferably at most 1 ppmw, more preferably at most 0.5 ppmw, more preferably at most 0.3 ppmw, and most preferably at most 0.1 ppmw, on the basis of total weight of the permeate. Such permeate may suitably be used as raw material in making a polyether polyol to be used in making slabstock polyurethane foam.

Further, preferably, the poly(propylene oxide) concentration in said permeate is from essentially zero to less than 1 ppmw, more preferably from essentially zero to 0.5 ppmw, more preferably from essentially zero to 0.3 ppmw, and most preferably from essentially zero to 0.1 ppmw, on the basis of total weight of the permeate. Such permeate may suitably be used as raw material in making a polyether polyol to be used in making either slabstock polyurethane foam or moulded polyurethane foam.

In particular, where propylene oxide is to be used in making moulded polyurethane foam, the concentration of poly(propylene oxide) having a molecular weight of 20,000 and higher, in such propylene oxide, should preferably not exceed 0.5 ppmw. More preferably, the concentration of said higher molecular weight poly(propylene oxide) is at most 0.4 ppmw. Preferably, the poly(propylene oxide) concentration in said retentate is from essentially zero to at most 20 ppmw, more preferably at most 10 ppmw, more preferably at most 5 ppmw, more preferably at most 3 ppmw, and most preferably at most 2 ppmw, on the basis of total weight of the retentate. Such retentate may suitably be used as raw material in making a polyether polyol to be used in making slabstock polyurethane foam.

Thus, a further advantage is that in addition to the permeate, the retentate can also have some end use value as long as the stage cut is properly controlled.

The membrane separation will be performed in a membrane unit, which comprises one or more membrane modules. Examples of suitable modules are typically expressed in how the membrane is positioned in such a module. Examples of these modules are the spirally wound, plate and frame (flat sheet), hollow fibres and tubular modules. Preferred module configurations are spirally wound and plate and frame. Most preferably, the non-porous or nanofiltration membrane is applied in a membrane unit, which comprises spirally wound membrane modules. These membrane modules are well known to the skilled person as for example described in Encyclopedia of Chemical Engineering, 4$^{th}$ Ed., 1995, John Wiley & Sons Inc., Vol 16, pages 158-164. Examples of spirally wound modules are described in for example U.S. Pat. Nos. 5,102,551, 5,093,002, 5,275,726, 5,458,774, 5,150,118, and WO2006040307.

It will be appreciated that preferably the operating temperature should be kept below the boiling point of the propylene oxide feed in order to have a liquid inlet stream. The boiling point of propylene oxide is about 34° C. Thus, at atmospheric pressure temperatures from 0° C. up to 34° C. may be applied. Suitably, the separation is carried out at a temperature in the range of from 5 to 30° C., more suitably at ambient temperature.

Step b) of the present process may be repeated multiple times, preferably two times. Such repetition implies the use of two or more membranes as described above arranged in series, wherein the permeate stream from the first membrane is sent to a second membrane, and wherein the permeate stream from the second membrane is recovered as a purified propylene oxide stream which may be sent to any third membrane as described above or to an adsorption bed in accordance with below-described optional step c). Such series of two or more membranes as described above may also be referred to as a so-called "membrane bank".

Optionally, the present process comprises step c) comprising sending the permeate stream resulting from step b) to an adsorption bed and recovering a purified propylene oxide stream from the adsorption bed.

The above-mentioned step c) is optional as the need for step c) depends on the quality (PPO concentration) of the filtrate stream resulting from step b) which in turn may depend on the feed to step a).

The adsorption bed to be used in optional step c) may comprise active carbon, silica, titania or zeolite powder.

Thus, advantageously, upon quality requirement, the already purified permeate stream coming from a first membrane having an average pore size of from 0 to 30 nm in above step b) can be treated in a second membrane separation step and/or in a compact adsorption step as in above step c). These additional steps will ensure highest purity, where needed.

The invention is illustrated by the process as shown in FIG. 1.

In the process as shown in FIG. 1, a stream 1 comprising propylene oxide, poly(propylene oxide) and particles having a particle size in the range of from 5 to 20 μm is sent to a filter unit 2 comprising a filtration screen having openings with an average diameter of at most 50 μm. The filtration screen is used as a self-cleaning filtration (SCF) screen, wherein the above-described back-wash cycle is applied. The retentate stream 3 from filter unit 2 may be used as raw material in making a polyether polyol to be used in making slabstock polyurethane foam. Part of retentate stream 3 may be split off and sent as recycle stream 4 to filter unit 2.

The filtrate stream 5 from filter unit 2 is sent to a first membrane module 6 comprising a membrane having an average pore size of from 0 to 30 nm. The permeate stream 7 from first membrane module 6 is sent to a second membrane module 8 comprising a membrane having an average pore size of from 0 to 30 nm. The permeate stream 9 from second membrane module 8 is recovered as a purified propylene oxide stream, which may advantageously be used as raw material in making a polyether polyol to be used in making either slabstock polyurethane foam or moulded polyurethane foam.

In case the purity of permeate stream 9 needs to be further increased, for example in the above-mentioned case of use in making moulded polyurethane foam, permeate stream 9 may be sent to an adsorption bed 10. From adsorption bed 10 a (further) purified propylene oxide stream 11 may be recovered.

Retentate streams 12 and 13 resulting from membrane modules 6 and 8, respectively, may advantageously be used as raw material in making a polyether polyol to be used in making slabstock polyurethane foam. Two or more of retentate streams 4, 12 and 13 may be combined before such use.

We claim:

1. Process for removing poly(propylene oxide) from propylene oxide, comprising:
   a) sending a stream comprising propylene oxide and poly(propylene oxide) to a filtration screen having openings with an average diameter of at most 50 μm, wherein the filtration screen is a self-cleaning filtration (SCF) screen; and
   b) sending the filtrate stream resulting from step a) to a membrane having an average pore size of from 0 to 30 nm and recovering a permeate stream from the membrane as a purified propylene oxide stream.

2. Process according to claim 1, wherein the average diameter of the openings of the filtration screen used in step a) is at most 25 μm and is at least 0.1 μm.

3. Process according to claim 1, wherein the self-cleaning filtration comprises a back-wash cycle.

4. Process according to claim 3, wherein the back-wash is initiated once the pressure of the fluid to be filtered on the retentate side of the filtration screen reaches a threshold.

5. Process according to claim 1, wherein step b) is repeated multiple times, wherein two or more membranes having an average pore size of from 0 to 30 nm arranged in series are used wherein the permeate stream from the first membrane is sent to a second membrane, and wherein the permeate stream from the second membrane is recovered as a purified propylene oxide stream which may be sent to any third membrane.

6. Process according to claim 1, additionally comprising:
   c) sending the permeate stream resulting from step b) to an adsorption bed and recovering a purified propylene oxide stream from the adsorption bed.

* * * * *